United States Patent
Gust et al.

(10) Patent No.: US 6,432,047 B1
(45) Date of Patent: Aug. 13, 2002

(54) ENDOSCOPIC SURGICAL PROCEDURES AND ENDOSCOPIC APPARATUS COMPRISING SEGMENTED FIBER OPTIC CABLES

(75) Inventors: Gary R. Gust, Huntington Beach, CA (US); B. Thomas Smith, Columbus; Steven B. Lovering, Yellow Springs, both of OH (US)

(73) Assignee: Micro Medical Devices, Inc., Elyria, OH (US)

( * ) Notice: Subject to any disclaimer, the term of this patent is extended or adjusted under 35 U.S.C. 154(b) by 0 days.

(21) Appl. No.: 09/257,897

(22) Filed: Feb. 25, 1999

(51) Int. Cl.[7] ............................. A61B 1/00; G02B 6/06
(52) U.S. Cl. ....................... 600/182; 600/132; 385/117
(58) Field of Search ................... 600/182, 112, 600/132, 133, 136, 172, 175, 160, 101; 385/116, 117, 55, 100

(56) References Cited

U.S. PATENT DOCUMENTS

| | | | |
|---|---|---|---|
| 4,327,738 A | * | 5/1982 | Green et al. ............ 600/109 |
| 4,862,873 A | * | 9/1989 | Yajima et al. ........... 600/111 |
| 5,101,468 A | | 3/1992 | Chiu |
| 5,411,500 A | * | 5/1995 | Lafferty et al. .......... 600/167 |
| 5,456,245 A | | 10/1995 | Bornhop et al. |
| 5,621,830 A | | 4/1997 | Lucey et al. |
| 5,680,492 A | | 10/1997 | Hopler et al. |
| 5,746,693 A | * | 5/1998 | Spitz et al. ............. 600/112 |
| 5,807,237 A | * | 9/1998 | Tindel ................... 600/114 |
| 5,812,719 A | | 9/1998 | Barry et al. |

FOREIGN PATENT DOCUMENTS

| | | |
|---|---|---|
| DE | 3914825 | 9/1990 |
| EP | 173110 | 3/1986 |
| FR | 1426646 | 4/1966 |
| WO | 9814812 | 4/1998 |

OTHER PUBLICATIONS

"Fiber–Optics Couple Arthroscope to TV", Langley Research Center, NASA Tech Briefs, Fall 1980.*

* cited by examiner

Primary Examiner—John P. Leubecker
(74) Attorney, Agent, or Firm—Fay, Sharpe, Fagan, Minnich & McKee, LLP

(57) ABSTRACT

A method of conducting endoscopic surgeries places the camera outside the sterile field, freeing the physicians hands and eliminating costs and inconveniences associated with sterilizing the camera between surgeries. Images may be relayed to the camera by means of a fiber optic cable. Cost issues associated with the long fiber optic cable are avoided by breaking it into two segments, only one of which is likely to be damaged during use. An image preserving connection is formed between the cable segments by a connector that fixes the ends of the cables in close proximity to one another, but a certain fixed distance apart. An image preserving connection is made between two fiber optic cables without the aide of a lens.

14 Claims, 4 Drawing Sheets

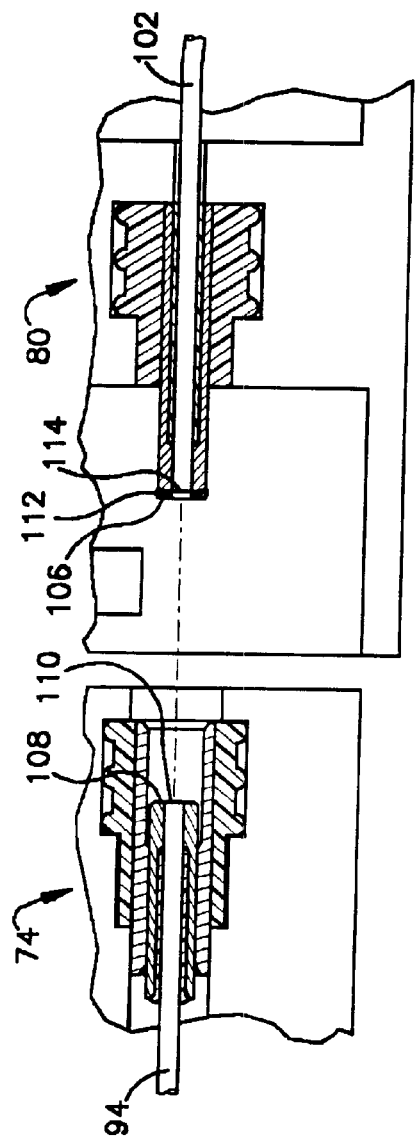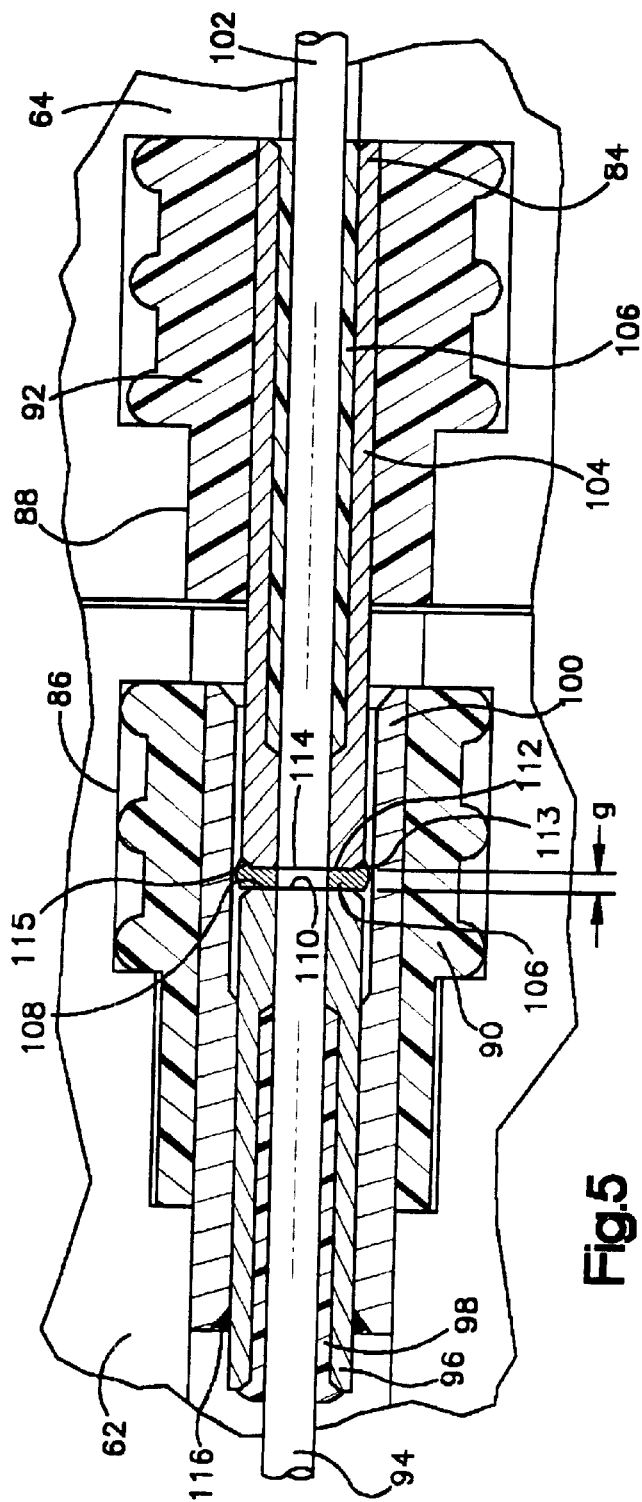

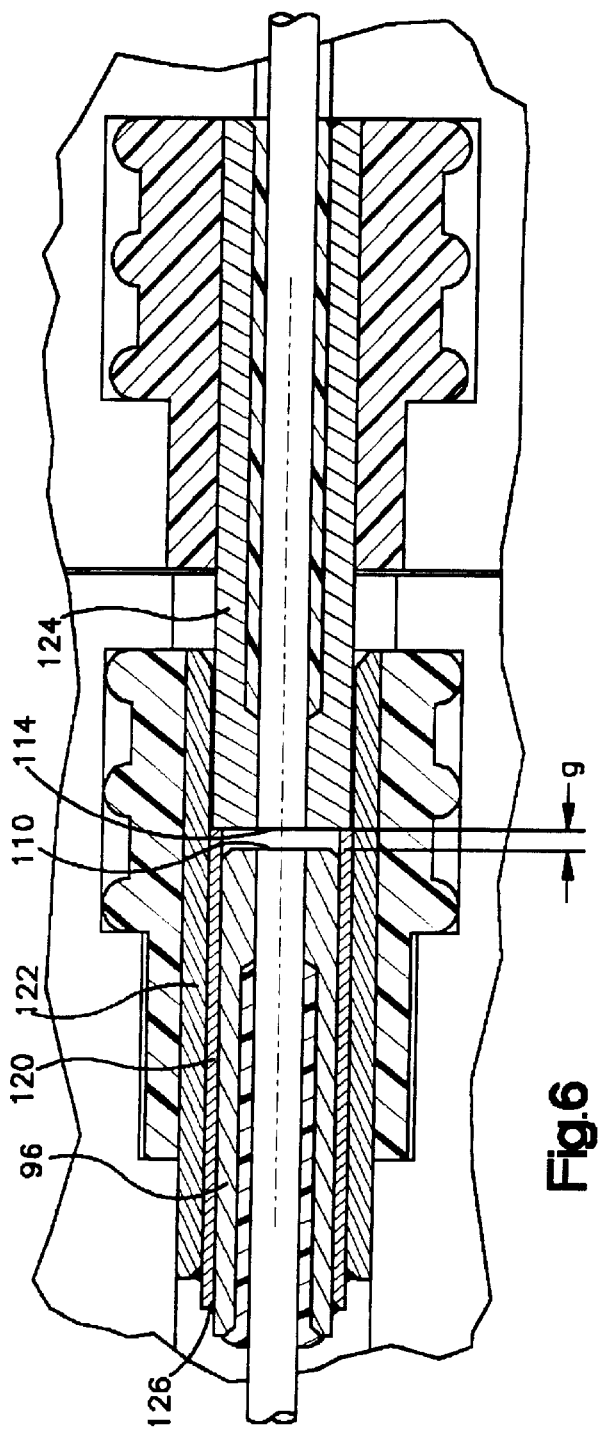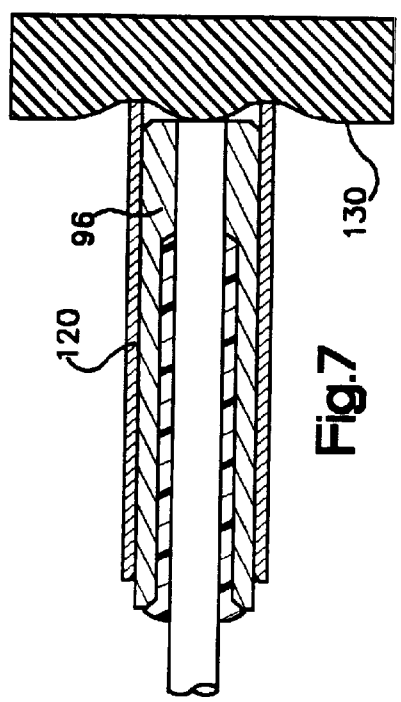

ENDOSCOPIC SURGICAL PROCEDURES AND ENDOSCOPIC APPARATUS COMPRISING SEGMENTED FIBER OPTIC CABLES

FIELD OF THE INVENTION

This invention arose in the field of endoscopic surgical devices but also pertains to the field of fiber optics.

BACKGROUND

There is great incentive to make endoscopes smaller. Smaller endoscopes make endoscopic surgeries less invasive and healing times shorter. If the endoscopes are small enough, the entire procedure can be carried out in a doctor's office, without general anesthetic, on an outpatient basis, resulting in a substantial cost savings. Today, most endoscopes in use are rigid endoscopes, comprising chains of lenses. An introducer at least 6 millimeters in diameter must be inserted in the patient's body to conduct surgery with the smallest of these. Applicants are working to develop flexible, serviceable, and affordable fiber optic endoscopes by means of which surgeries may be conducted through an introducer 2 millimeters or less in diameter.

In a typical endoscopic surgery, the introducer is a cannula with a trocar through its center, which is inserted into the patient's joint. The trocar is then withdrawn and the endoscope inserted. The endoscope is connected to a camera through an adapter that clips on to the base of the endoscope. A wire from the camera carries the image to a video processor.

The person conducting the surgery holds the camera while manipulating the endoscope. Although orthopedic surgeons have become used to holding cameras while conducting these surgeries, relieving them of this burden could only enhance their ability to conduct them.

An important issue in conducting surgeries of this type is maintaining sterile conditions. For this purpose, a sterile field is created. A sterile field is an area around the point of incision that is prepared before a surgical procedure and maintained during the procedure. The preparation and maintenance of a sterile field is described in Atkinson and Fortunato, Berry & Kohn's Operating Room Technique (8th ed. 1996). All items within the sterile field must be sterilized. In prior art endoscopic surgeries, the camera, wire, and adapter are within the sterile field. Federal regulations and good practice therefore require these parts to be sterilized between uses. This is inconvenient, time consuming, and reduces the availability of the apparatus for use in other surgeries. Furthermore, the sterilization procedure can damage the electronic components.

SUMMARY OF THE INVENTION

In one respect, the present invention comprises a method of conducting endoscopic surgery in which the camera is outside the sterile field. According to this method, the camera is placed outside the sterile field and the image is transmitted to the camera by a fiber optic cable. Preferably, the apparatus for conducting the surgery is organized so that the person conducting the surgery does not have to hold the camera while manipulating the endoscope.

The inventors observed that use of a single long fiber optic cable to carry the image outside the sterile field would makes this procedure expensive. The initial cost of such a cable would be high and even with care it is inevitable that it would be damaged during use. The cable would probably not last through ten surgeries.

To ameliorate this expense, the inventors developed a segmented fiber optic cable. By a segmented fiber optic cable, applicants mean an image transmitting fiber optic cable formed by the union of two or more separate fiber optic cables. Applicants observed that a short segment of the cable nearest the patient is the portion most likely to be damaged during use. In a segmented fiber optic cable, this portion (called the "disposable cable portion", although it may be used several times) may be replaced while the longer portion of the cable (the "reusable cable portion") continues to be reused. The reusable cable portion can also be armored. While such armoring on the disposable cable portion might interfere with the operation of the endoscope and would, in any case, excessively increase the diameter of the introducer, armoring on the reusable cable portion presents no disadvantages. An armored reusable cable portion is expected to withstand upwards of a hundred surgeries.

In developing a segmented fiber optic cable, the inventors were faced with the problem of connecting the segments in a way that would preserve the image quality required for surgical procedures. Fiber optic cables comprise bundles of optical fibers. Thousands of fibers are required to form a satisfactory image. Image preserving connections between such bundles of image transmitting fibers appear to have been unknown prior to applicant's invention. By an image preserving connection, applicants mean a connection across which simple images, such as those of grids, that do not push the resolution limits of the image conveying apparatus, are not degraded beyond recognition. Applicants have invented an image preserving fiber optic cable connector that preserves images to the degree required for endoscopic surgery.

Applicants' preferred connector functions by holding the tips of the fibers a certain small distance apart. It was unexpected that two fiber optic cables could be connected in this way. If the fibers were butted against one another, the image would suffer from fixed pattern noise, giving the image a mottled appearance and making it essentially useless. If the fibers were too far apart, the image would be blurred. Applicants unexpectedly discovered that there is a fiber tip spacing that allows the image to be transferred without noticeable fixed pattern noise, substantial loss of resolution, or excessive loss of image quality.

Applicants endoscopic surgical apparatus is expected to change the economics that affect the way endoscopic surgeries are performed. By placing the camera outside the sterile field, the expense and damage associated with sterilizing the camera can be avoided. By using a segmented fiber optic cable, the expenses associated with the cable itself can be kept under control. If the connection between the cable segments is made, according to applicants' preferred embodiment, using a connector that functions by holding the ends of the cables a small distance apart, rather than by means of a lens, problems associated with connector itself will not present problems comparable to those that were associated with a camera within the sterile field.

Applicants' invention is also expected to have a direct effect on the mechanics of endoscopic surgeries. The person conducting the procedure will no longer have to hold the camera, allowing greater control of the endoscope. In conjunction with other advances made by applicants, the invention is expected to contribute to the adoption of small diameter fiber optic endoscopes, which will mean less invasive surgeries, surgeries that can be performed on smaller joints, and surgeries that no longer have to be performed in a hospital.

BRIEF DESCRIPTION OF THE DRAWINGS

FIG. 4 shows a preferred fiber optic cable image transmitting sub-connector with the two portions disconnected.

FIG. 5 shows the fiber optic cable image transmitting sub-connector of FIG. 4 with the two portions connected.

FIG. 6 shows another example of a fiber optic cable image transmitting sub-connector.

FIG. 7 demonstrates a method of setting the gap during assembly of the sub-connector of FIG. 6.

DETAILED DESCRIPTION

In one embodiment, applicants invention is an endoscopic surgical technique that places the camera outside the sterile field. Preferably the image is transmitted to the camera using a segmented fiber optic cable. Preferably, the fiber optic cable, with sheath, is four millimeters in diameter or less, more preferably 1.4 millimeters in diameter or less. In another embodiment, the invention is a method of conducting surgeries using a segmented fiber optic cable to transmit an image from within a patient's body to where it can be viewed by a person conducting the surgery.

A method of conducting multiple surgeries in accordance with the present invention treats one end of the cable, the one nearest the patient, as being disposable or interchangeable. For example, the end of the cable nearest the patient may be separated from the rest of the cable and sterilized between one surgery and the next. Alternatively, the end of the cable nearest the patient may be disposed of and replaced between one surgery and the next.

Figure 1:
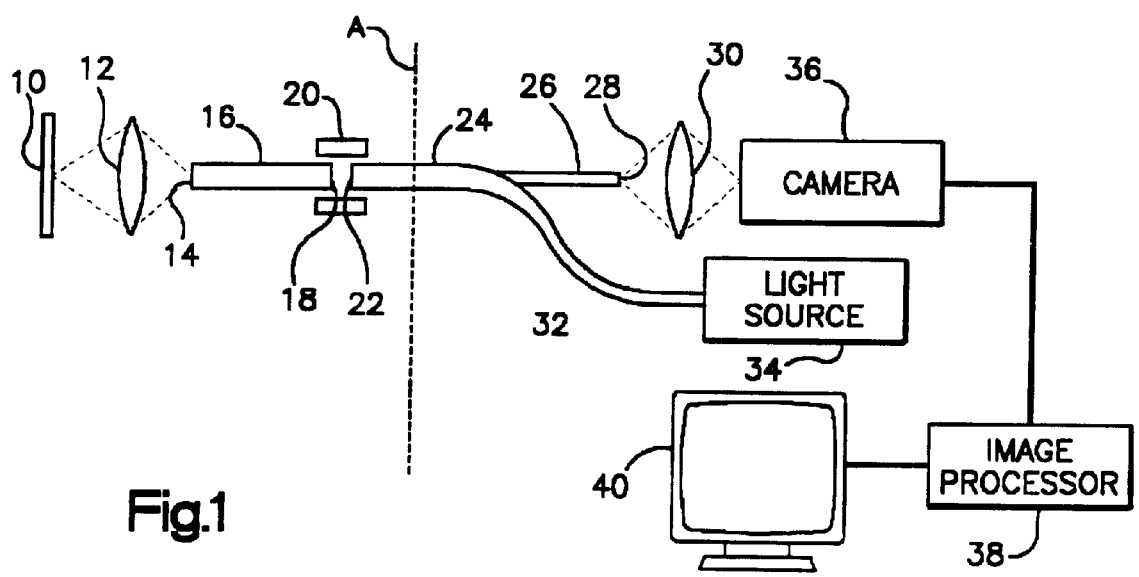
FIG. 1 is a schematic of a preferred endoscopic surgical apparatus comprising a segmented fibre optic cable.

A preferred apparatus for conducting endoscope surgeries in accordance with the invention is shown schematically in FIG. 1. It comprises a lens 12, a disposable fiber optic cable 16, a connecter 20, a reusable fiber optic cable 24, a camera 36, an image processor 38, a monitor 40, and an illumination light source 34. The illuminating light is generally transmitted to the target area 10 through a set of fibers 32 that are bundled with, but separate from, the image transmitting fibers 26. As described in co-pending application Ser. No. 08/890,803, which is incorporated herein by reference, it is also possible to combine the functions of channeling illuminating light and image light in one set of fibers thereby further reducing the size of the device that must be inserted in the patient.

In operation, the lens 12 gathers an image from a target area 10 illuminated by light channeled from light source 34. The lens 12 directs the image into the polished ends of the fibers at one end 14 of disposable fiber optic cable 16. Light is transmitted down the length of the fibers to the other end 18 of the disposable fiber optic cable 16. The light within each fiber of the cable comprises a single point of image data. The data from a group of fibers must be in proper spacial relation for an image from one cable end to form at the other end. The disposable fiber optic cable 16 is a coherent optical fiber bundle, in that the spacial relationship between the fibers is the same at both ends of the cable. Thus an image of the target area 10 appears at the end 18 of the disposable fiber optic cable 16.

In the preferred embodiment, the image from the end 18 of the disposable fiber optic cable 16 falls directly upon the end 22 of the reusable fiber optic cable 24. Alternatively, the connector 20 could comprise a lens that directs the image from the end 18 onto the end 22. Such a lens would need to be somewhat out of focus to avoid fixed pattern noise. The reusable fiber optic cable 24 channels the image to the lens 30 associated with camera 36.

The camera 36 generates a signal coding the image. The signal coding the image is transferred from the camera 36 to the image processor 38. The image processor 38 contains software and operates to remove artifacts from the image and enhance it. The output of the image processor 38 is displayed on the monitor 40. The delay in processing the image is minimal, so that the image displayed is current with the image being gathered by the lens 12. In other words, the image displayed is a real time image.

When, as in the preferred embodiment, the apparatus comprises a segmented fiber optic cable, a fiber optic cable connector is necessary. For surgical applications, the connector is preferably small, easy to operate, and essentially fool proof. Ideally, the connector should operate to form an image transmitting connection between the cables when the two ends of the connector are pushed together with a minimum of force. If the connector is of the type that requires the ends to be oriented correctly in terms of rotations about the cable axes, the two ends of the connector should provide both visual and tactile indications as to the correct orientation.

The preferred connector is one that can hold the ends of the cables a fixed distance apart. Theoretically, the connection could be made using a lens. Lenses have a number of drawbacks however, which drawbacks relate to the logistics of aligning the lens and the fibers with sufficient precision and the trade-offs that must be made between size of the lens, its precision, and its cost.

Figure 2:
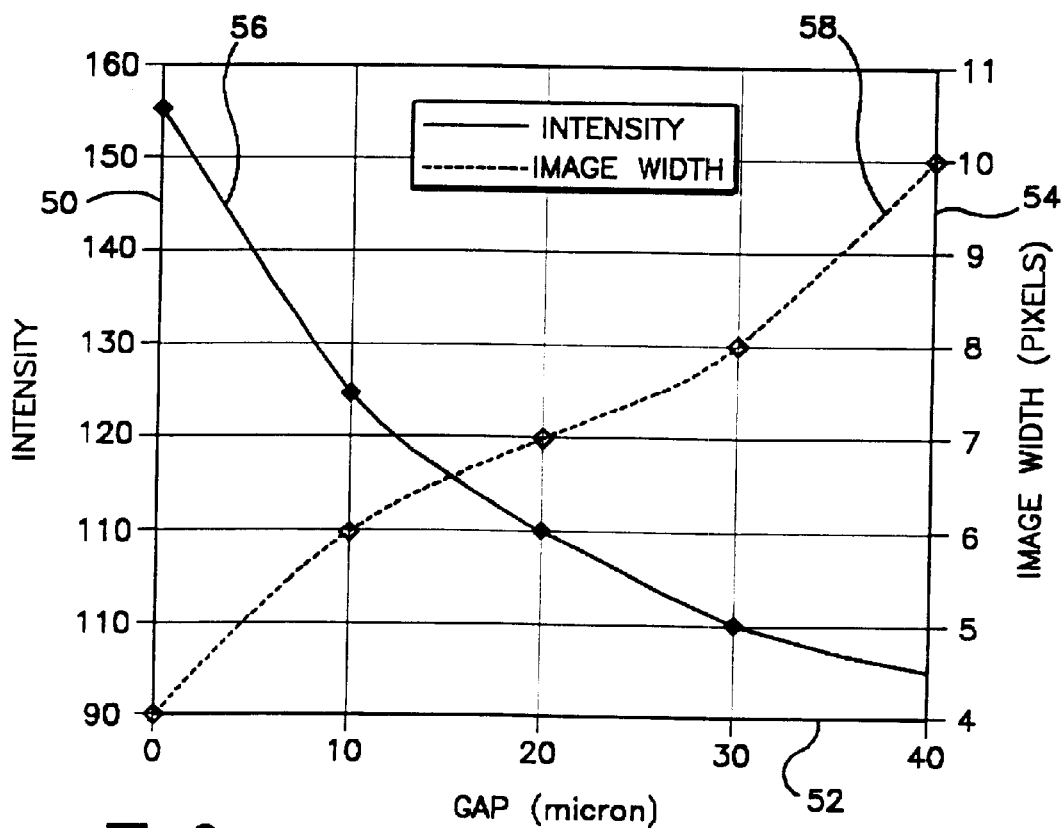
FIG. 2 is a plot showing how the width and intensity of an image of a line vary with the gap between the ends of two fiber optic cables.

Applicants have experimentally determined the positioning required to form an image preserving connection between the ends of two 1.0 millimeter diameter fiber optical cables each having 30,000 close packed fibers, each fiber having a diameter of approximately 4 micrometers and a numerical aperture of approximately 0.35. The solid line 56 in FIG. 2 plots the variation of intensity 50 of an image, which is that of a line, with a gap 52 between the cable ends. By cable ends, the applicants mean the surfaces formed by the ends of the fibers of the cables when the ends of the cables have been polished. The dashed line 58 plots the variation of the image width 54 with the gap 52. The width of the line's image is a measure of the image resolution. Resolution was deemed adequate for medical diagnostic purposes when the gap was 20 micrometers or less, although resolution was noticeably better when the gap was 10 micrometers or less. When the gap was essentially zero, the image suffered from severe fixed pattern noise. This fixed pattern noise decreased to a satisfactorily low level when the gap was increased to 4 micrometers. The optimal gap was 4 to 8 micrometers. The offset of the axes of the two cables is preferably also controlled to some degree. Preferably, the offset is not more than 10 micrometers.

The preferred gap between cable ends is expected to vary proportionally with fiber diameter and inversely proportionally with numerical aperture, at least for small numerical apertures. As a first approximation, the applicants suggest that, when working with fibers having substantially different diameters and/or numerical apertures from the ones used in the examples given here, the gap be selected in the range:

$$.35\frac{d}{NA} < g < .70\frac{d}{NA}$$

where g is the gap, d is the mean fiber diameter for the two cables, and NA is the numerical aperture of the cable from which the image is to be transmitted. Ultimately, however, the ideal gap may need to be determined empirically.

Figure 3:
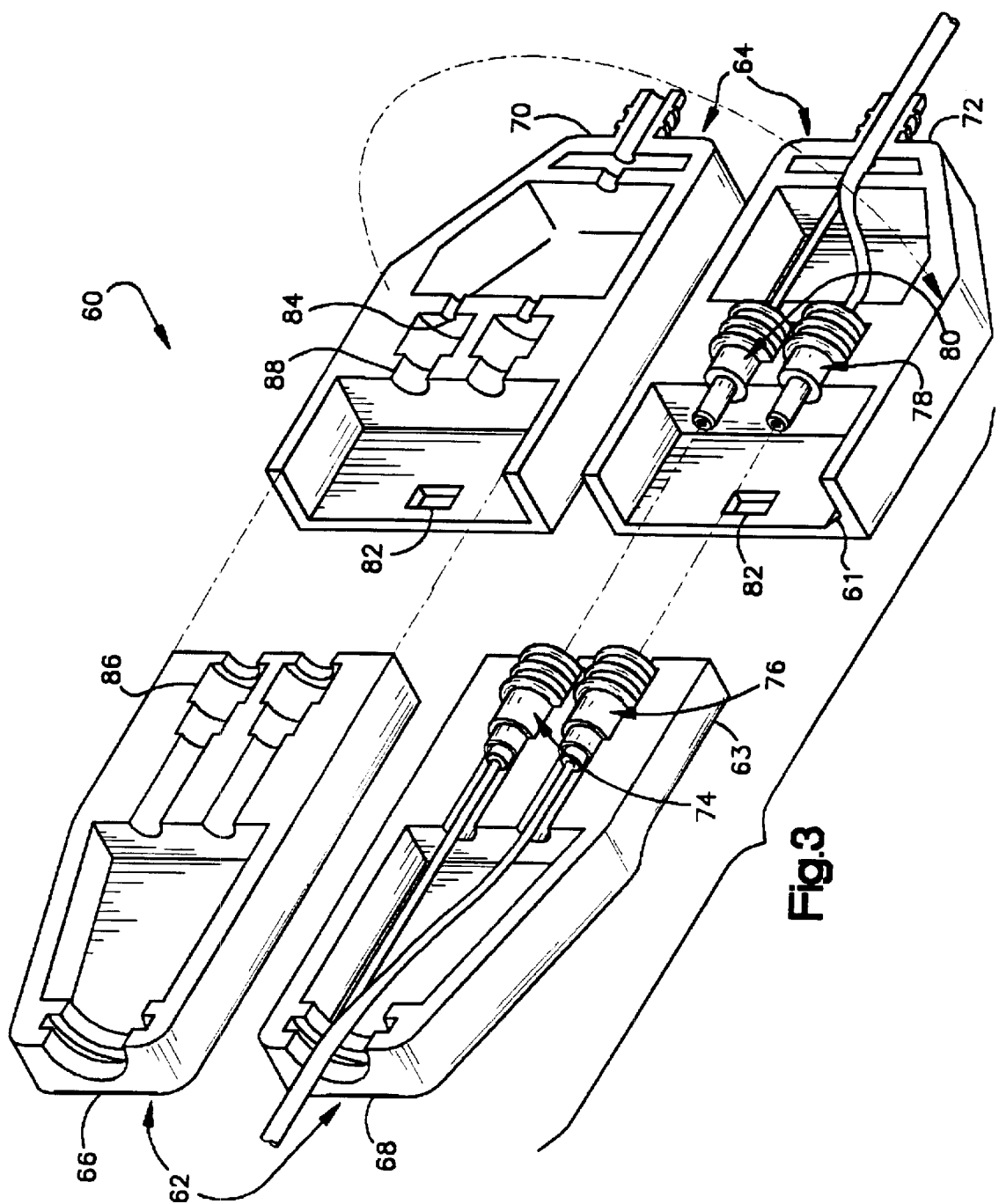
FIG. 3 is an exploded isometric view of a preferred fiber optic cable connector that connects both image transmitting fibers and illumination transmitting fibers.

A preferred connector in accordance with the present invention is shown disassembled in FIG. 3. The connector 60 comprises two housing ends 62 and 64. The end 62 shown on the left hand side of FIG. 3 comprises connector housing portions 66 and 68, which contain sub-connector ends 74 and 76. The other end 64 comprises connector housing portions 70 and 72, which contain sub-connector ends 78 and 80. Sub-connector ends 74 and 80 form and an image transmitting sub-connector. Sub-connector ends 76 and 78 form an illumination transmitting sub-connector. Connector end 62 slides within connector end 64. Shaped corners 61 and 63 key the two connector ends so they cannot be joined unless they are properly oriented. The ends are reversibly held together by protrusions (not shown) that snap into notches 82.

A detailed example of a preferred image transmitting sub-connector is shown in FIGS. 4 and 5. The female portion 74 comprises a fiber bundle 94 surrounded by a stainless steel ferrule 96. The fiber bundle 94 is bound to the ferrule 96 by epoxy 98. The male portion comprises a cable fiber bundle 102 surrounded by ferrule 104 and bound to it by epoxy 106. The ends 108 and 112 of the ferrules 96 and 104 are flush with the polished ends 110 and 114 of the fiber bundles 94 and 102.

The female end fiber ferrule 96 is positioned concentrically within an alignment tube 100. A tack 116 prevents the alignment tube 100 from sliding relative to the ferrule 96. The alignment tube 100 helps guide and axially align the fiber bundle ends 100 and 114 together when the male and female portions of the connector are being joined.

The alignment tube 100 is itself positioned within an elastic member 90, which fits tightly within the connector housing 62 in the region 86. The elastic member 90 functions to allow the fiber bundle 94 to move freely in the direction of its axis relative to the connector housing 62. The elastic member 90 also exerts a biasing force tending to press the fiber bundle ends 110 and 114 together when the two ends 62 and 64 of the connector 60 are joined. Displacement of the end 114 of the male fiber bundle 102 is resisted by the male end ferrule 104, which rests against the housing end 64 at the point 84.

The male end ferrule 104 is positioned concentrically within elastic member 92. Elastic member 92 fits tightly within connector housing 64 in the region 88. The elastic member 92 allows the fiber bundle 102 to move in directions perpendicular to its axis.

A spacer 106 is formed by electroplating on the end 112 of the male end ferrule 104. The spacer 106 fixes the gap between the fiber bundle ends 110 and 114 when the ends of the connector are joined. One of the advantages of forming a spacer by electroplating is that an electroplating-formed spacer compensates for the rounding that tends to occur around the perimeters 113 and 115 of the ferrule ends. FIGS. 4, 5, 6, and 7 are not drawn to scale in that the gap is much narrower, and the spacer much thinner, than shown in these illustrations.

In the preferred embodiment, the illumination transmitting sub-connector is the same as the image transmitting sub-connector, except that the illumination transmitting sub-connector does not have a spacer.

Another example of a sub-connector in accordance with the invention is shown in FIG. 6. In this example, there is an extension sleeve 120 between the female end ferrule 96 and the alignment tube 122. When the male and female ends of this sub-connector are joined, the extension sleeve 120 meets the male end ferrule 124 and maintains the gap between the fiber bundle ends 110 and 114. In this embodiment, the male end ferrule 124 has a larger diameter than the female end ferrule 96. In assembling the connector with the extension sleeve, the gap can be set, as illustrated in FIG. 7, by pressing the female end ferrule 96 and the extension sleeve 120 against a shaped rubber surface 130 and sliding the extension sleeve to conform to the surface. When the extension sleeve is correctly positioned, a tack weld 126 can be used to fix it in place.

When a segmented fiber optic cable is used, the portion of the cable which does not have to fit in the cannula can be armored. A preferred method of armoring is by enclosing the cable in a relatively thick metal sheath.

A surgical apparatus constructed and operated in conformity with one or more of the preferred embodiments described above will provide convenient and cost effective means with which surgical procedures can be conducted in accordance with the applicants invention. These procedures solve important sterilization problems and contribute to the practicability of minimally invasive surgeries using fiber optics.

We claim:

1. An apparatus for conducting endoscopic surgeries, the apparatus comprising:
   a distal fiber optic cable;
   a lens positioned to direct images into one end of the distal fiber optic cable;
   a proximal fiber optic cable;
   a connector for attaching the distal and proximal fiber optic cables, the connector forming an image preserving connection between the distal and proximal fiber optic cables without the aid of a lens by maintaining the ends of fibers at one end of the proximal fiber optic cable in proximity to, but some distance apart from, the ends of fibers at one end of the distal fiber optic cable;
   a camera for receiving images from the proximal fiber optic cable; and,
   a monitor for displaying images from the camera.

2. An apparatus as in claim 1, wherein:
   the connector comprises a spacer that is positioned such that when the connector is operating to form a connection, the spacer resides between ferrules on the distal and proximal fiber optic cables and maintains the spacing between the fiber ends.

3. An apparatus as in claim 1, wherein:
   each connector end comprises a ferrule that surrounds fibers of the cable to which the connector end is attached, each ferrule having an end that is flush with the ends of the fibers it surrounds, one of the ferrules being surrounded by an extension sleeve that extends slightly beyond the flush end of the ferrule, the extension sleeve functioning to maintain the spacing between the fiber ends when the two ends of the connector are joined.

4. The apparatus as in claim 1, further including:
   a first connector end attached to the distal fiber optic cable and a second connector end attached to the proximal fiber optic cable, the connector connecting the first and second connector ends.

5. An apparatus for conducting endoscopic surgery, the apparatus comprising:

a distal fiber optic cable;

a lens disposed at one end of the distal fiber optic cable;

a proximal fiber optic cable;

first and second ferrules surrounding ends of the distal and proximal optical cables, respectively, the ferrules having ends that are flush with the ends of the fibers the ferrules surround;

a connector which connects the ferrules of the distal and proximal fiber optic cables, the connector including a spacer disposed between the ferrules to maintain a distance between the fiber ends of the distal and proximal optical cables;

a camera for receiving images from the proximal fiber optic cable; and, a monitor for displaying images from the camera.

6. An endoscopic apparatus comprising:

a distal optic cable for transmitting images from a first end to a second end;

a proximal fiber optic cable for transmitting images from a first end to a second end;

a first connector end attached to the distal fiber optic cable second end;

a second connector end attached to the proximal fiber optic cable first end;

a connector which optically connects the distal optic cable second end and the proximal optic cable first end to form an image preserving connection between the distal and proximal optic cables;

an alignment tube functioning to help guide the optical cable ends into proximity with one another as the two optical cable ends are received in the connector;

a camera for receiving images from the proximal optic cable; and, a monitor for displaying images from the camera.

7. An endoscopy apparatus comprising:

a distal optic cable having an optical image receiving first end;

a proximal optic cable;

a connector which optically connects the distal and proximal optic cables, the connector including a housing with apertures for receiving ends of the distal and proximal optic cables;

an elastic member positioned between at least one of the optic cable ends and the connector housing, the elastic member allowing freedom of movement of the optic cable relative to the connector housing;

a camera for receiving images from the proximal optic cable; and, a monitor for displaying images from the camera.

8. A method of conducting endoscopic surgeries using a plurality of sterile disposable segments used inside a sterile surgical field and a reusable segment extending outside the sterile field to associated video equipment, the method comprising:

connecting a first of the sterile disposable optic cable segment to the reusable optical cable segment;

performing a first surgery on one patient using the first disposable optic cable segment to view interior regions of the patient;

disconnecting the first disposable optic cable segment from the reusable optic fiber segment;

connecting a different sterile disposable optic cable segment to the reusable optic cable segment; and performing a second surgery using the another disposable optic cable segment and the original reusable optic cable segment, such that the reusable optic cable segment is reused in subsequent surgeries and the disposable optic cable segment is replaced for each surgery.

9. The method of conducting endoscopic surgeries as in claim 8 further including:

connecting a video camera to the reusable optic cable segment outside the sterile field, the camera remaining connected to the reusable optic cable segment and being used in the subsequent surgeries.

10. A method of conducting surgery comprising:

connecting a distal optical cable segment to a proximal optical cable segment, the two segments being connected in a manner that maintains the ends of the two optical cable segments close to each other, but a small distance apart, and wherein images are transmitted between the two segments without passing through a lens;

optically transmitting an image from within a patient's body in a sterile field through the distal and proximal optical cable segments;

transmitting the image to a monitor outside the sterile field that displays the image as the surgery progresses such that a person conducting the surgery can view the monitor while conducting the surgery.

11. The method of conducting surgery as in claim 10, wherein:

the distal optic cable segment, including a surrounding sheath, is less than 2 millimeters in diameter where it enters the patient's body.

12. The method of conducting surgery as in claim 10, further including:

after the surgery, disconnecting the distal optical cable segment, connecting another sterile distal optical cable segment to the proximal optical cable segment and displaying images on the monitor while another surgery is performed.

13. A method of conducting surgery comprising:

using a segmented fiber optic cable to transmit an image from within a patient's body to where it can be viewed by a person conducting the surgery, the cable having at least one connector that functions to maintain fibers at the end of one segment of the cable between four and twenty micrometers from fibers at the end of another segment of the cable.

14. The method of conducting surgery as in claim 13, wherein:

at least one segment of the cable is armored to a greater extent than at least one other segment of the cable.

* * * * *